United States Patent [19]
White et al.

[11] 4,427,676
[45] Jan. 24, 1984

[54] THIOMORPHOLINE DERIVATIVES

[75] Inventors: Alan C. White, Windsor; Michael M. Hann, Maidenhead, both of England

[73] Assignee: John Wyeth & Brother Ltd., Maidenhead, England

[21] Appl. No.: 330,618

[22] Filed: Dec. 14, 1981

[30] Foreign Application Priority Data

Dec. 19, 1980 [GB] United Kingdom ............... 8040826

[51] Int. Cl.³ ................... C07D 279/12; A61K 31/54
[52] U.S. Cl. ..................................... 424/246; 544/59; 544/60; 544/58.1; 544/58.7; 544/58.2
[58] Field of Search .................... 544/58, 59, 60, 58.2, 544/58.1; 424/246

[56] References Cited

U.S. PATENT DOCUMENTS 2,363,330  11/1944  Jackson et al. .................... 544/59
2,375,628   5/1945  D'Alelio et al. .................... 544/59

OTHER PUBLICATIONS

Siegmund et al., Proc. Soc. Exp. Biol. Med., vol. 95, pp. 729–731 (1957).
Aceto et al., Brit. J. Pharmac., vol. 36, pp. 225–239 (1969).

*Primary Examiner*—John M. Ford
*Attorney, Agent, or Firm*—Arthur G. Seifert

[57] ABSTRACT

The invention provides novel thiomorpholines of the formula (I)

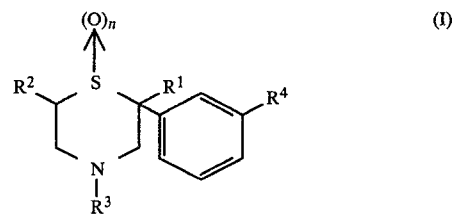

and their pharmaceutically acceptable acid addition salts wherein n represents 0 or 1, $R^1$ represents (lower)alkyl, $R^2$ represents hydrogen or (lower)alkyl, $R^3$ represents hydrogen, lower alkyl, lower alkenyl, lower alkynyl, aryl(lower)alkyl, 2-tetrahydrofurylmethyl or cycloalkylmethyl and $R^4$ represents hydrogen, hydroxy, acyloxy or a protected hydroxy group, with the proviso that when n is 0, $R^4$ is other than hydrogen. The compounds in which n is 0 and $R^4$ is lower alkoxy, hydroxy or acyloxy are analgesics and/or opiate antagonists and the compounds in which n is 1 and $R^4$ is hydrogen are hypotensives or anti-hypertensives. The other compounds of formula (I) are intermediates for the pharmacologically active compounds.

17 Claims, No Drawings

THIOMORPHOLINE DERIVATIVES

This invention relates to thiomorpholine derivatives, to process for their preparation and to pharmaceutical compositions containing them.

The present invention provides novel thiomorpholine derivatives of the general formula (I)

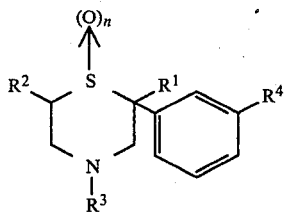

and their pharmaceutically acceptable acid addition salts. In this formula n represents 0 or 1, $R^1$ represents (lower)alkyl, $R^2$ represents hydrogen or (lower)alkyl, $R^3$ represents hydrogen, lower alkyl, lower alkenyl, lower alkynyl, aryl(lower)alkyl, 2-tetrahydrofurylmethyl or cycloalkylmethyl and $R^4$ represents hydrogen, hydroxy, acyloxy or a protected hydroxy group such as lower alkoxy, benzyloxy or (lower)alkoxymethoxy, with the proviso that when n is 0, $R^4$ is other than hydrogen.

The term "lower" as used herein means that the radical referred to contains 1 to 6 carbon atoms. The radical preferably contains 1 to 4 carbon atoms. For example, when any of the groups $R^1$, $R^2$ and $R^3$ is a lower alkyl group the radical may be, for example, methyl, ethyl, propyl or butyl. When $R^3$ is lower alkenyl or lower alkynyl suitable groups include, for example, allyl, 2-methyl-2-propenyl, 3-methylbut-2-enyl and propynyl. When $R^3$ is cycloalkylmethyl the group is preferably cyclopropylmethyl or cyclobutylmethyl. When $R^3$ is aryl(lower)alkyl the group can be, for example, benzyl or phenethyl. When $R^4$ is acyloxy it is preferably a lower alkanoyloxy group such as acetoxy, propionyloxy or butyryloxy. When $R^4$ is protected hydroxy suitable groups include alkoxy (such as lower alkoxy e.g. methoxy, ethoxy, propyloxy, butyloxy), benzyloxy and (lower) alkoxymethoxy (e.g. methoxymethyl).

A preferred $R^1$ group is ethyl and a preferred $R^3$ group is lower alkyl, preferably methyl. Preferably $R^4$ is a hydroxy group.

When n is 0 the compound of the invention are thiomorpholine derivatives of the general formula (Ia)

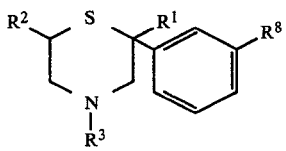

and their pharmaceutically acceptable acid addition salts, wherein $R^1$, $R^2$ and $R^3$ are as defined above and $R^8$ represents hydroxy, acyloxy or a protected hydroxy group.

When n is 1 the compounds of the invention are sulphoxide derivatives of the general formula (Ib)

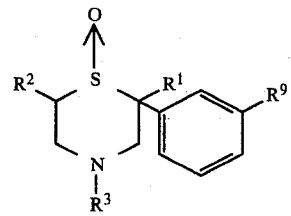

and their pharmaceutically acceptable acid addition salts, wherein $R^1$, $R^2$ and $R^3$ are as defined above and $R^9$ represents hydrogen, hydroxy, acyloxy or a protected hydroxy group.

The compounds of the invention where n is 0 may be prepared by deoxygenating a sulphoxide of general formula Ib or an acid addition salt thereof and, if desired, where in the product the group $R^3$ or $R^4$ is not the group required converting such a group into the required group.

Processes for deoxygenating sulphoxides are known in the literature and the particular process chosen can depend upon the stereochemistry of the sulphoxide derivative. For example sulphoxides of 1R*, 2S*, 6R* configuration may be deoxygenated by known deoxygenating agents such as triphenylphosphine (e.g. in carbon tetrachloride), iodotrimethylsilane, lithium aluminium hydride/titanium (IV) chloride and lithium aluminium hydride/aluminium chloride. However, it is preferred to use only the more vigorous reagents such as lithium aluminium hydride/titanium (IV) chloride or lithium aluminium hydride/aluminium chloride when the sulphoxides have the 1R*, 2R*, 6R* configuration. If the sulphoxides are mixture of isomers of different relative configuration then the choice of deoxygenation reagent can affect the proportion of the isomers in the product.

The sulphoxides of general formula (Ib) where $R^2$ is lower alkyl and their acid addition salts may be prepared by C-alkylating a sulphoxide of general formula

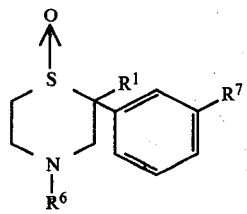

or an acid addition salt thereof, wherein $R^1$ has the meaning given above, $R^6$ is (lower)alkyl or aryl(lower) alkyl and $R^7$ is hydrogen or a protected hydroxy group and, if desired, where in the product the group $R^3$ or $R^9$ is not the group required converting such a group into the required group. The C-alkylation may be effected with an alkylating agent in the presence of an amide base or other strong bases such as alkyl lithium or potassium hydride. The alkylating agent may be, for example, a lower alkyl halide, sulphate or tosylate or a tri(-lower)alkylphosphate. Examples of amide bases are lithium diisopropylamide, lithium tetramethylpiperidine, and N-tertiarybutylcyclohexylamide or other compounds of formula MA where M is sodium, potassium or lithium and A is a secondary amine radical. The amide base may be formed in situ by reaction of a metal compound MR (where M is sodium, potassium or lithium and R is alkyl, aryl or aralkyl) with a secondary amine.

The sulphoxides of general formula (Ib) where $R^2$ is hydrogen and their acid addition salts (in particular the compounds of general formula II) may be prepared by alkylating a sulphoxide of general formula (III)

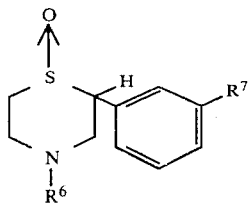

or an acid addition salt thereof where $R^6$ and $R^7$ are as defined above and, if desired, where in the product the group $R^3$ or $R^9$ is not the group required converting such a group into the required group.

The alkylation of the sulphoxide (III) to the sulphoxide (Ib) can be carried out using alkylating agents (as mentioned above) in presence of amide bases (as mentioned above) or other strong bases such as alkyl lithium or potassium hydride. The reagent used can affect the proportion of the different isomers of structure (Ib) in the product. For example we have found that, in general, alkylation of (III) with a tri(lower)alkylphosphate such as triethylphosphate (with an amide base such as lithium diisopropylamide) gives the product (Ib) substantially with the $1R^*, 2R^*$ configuration. On the other hand alkylating agents such as alkyl halides and tosylates tend to give product (Ib) mainly in the form having the $1R^*, 2S^*$ configuration but with a minor amount of isomer having the $1R^*, 2R^*$ configuration. If desired a mixture of isomers can be separated by standard procedures or the mixture can be subjected to the further processes described above and the mixture of resulting compounds (I) can be separated.

The sulphoxides of general formula (III) may be prepared by oxidation of compounds of general formula (IV)

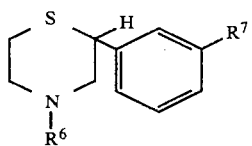

or acid addition salts thereof, where $R^6$ and $R^7$ have the meanings given above. The oxidation may be effected by, for example, reacting an acid addition salt of the compound of formula IV with a peracid such as 3-chloroperbenzoic acid or monoperphthalic acid or with an alkali metal periodate.

The compound of the invention where n is 0 and $R^2$ represents hydrogen may be prepared by an alternative process which comprises alkylating a compound of general formula (IV) or an acid addition salt thereof. For example a compound of general formula (IV) or an acid addition salt thereof may be alkylated to a compound of the invention using an alkylating agent such as an alkyl halide, tosylate or sulphate in the presence of an amide base or a strong base (as exemplified above).

Where in any of the processes described above a compound of the invention is obtained in which the $R^3$ or $R^4$ group is not the group required such a group may be converted to the required group by known processes. For example compounds in which $R^3$ is hydrogen may be prepared by dealkylating a compound in which $R^3$ is lower alkyl, particularly methyl, e.g. by reaction with ethyl-, phenyl-, vinyl- or 2,2,2-trichloroethylchloroformate followed by removal of the resulting N-substituent with, for example, dilute acid or zinc and acetic acid or basic conditions as appropriate. Compounds in which $R^3$ is hydrogen may also be prepared by hydrogenolysis of a compound in which $R^3$ is benzyl. A compound in which $R^3$ is hydrogen may be "N-alkylated" to a compound in which $R^3$ is lower alkyl, lower alkenyl, lower alkynyl, aryl(lower)alkyl, tetrahydrofurylmethyl or cycloalkylmethyl. In one method of "N-alkylation" a compound in which $R^3$ is is hydrogen may be reacted with a lower alkyl halide, a lower alkenyl halide, a lower alkynyl halide, an aryl (lower)alkyl halide, a tetrahydrofurylmethyl halide or a cycloalkylmethyl halide in presence of an acid acceptor (e.g. an alkali metal carbonate), preferably in solution in an organic solvent. An alternative method of "N-alkylation" comprises treatment of the N-unsubstituted compound with an aldehyde and sodium cyanoborohydride or with an aldehyde and hydrogen in presence of a hydrogenation catalyst. A preferred method of cycloalkylmethylating involved reacting the N-unsubstituted compound with a cycloalkylcarbonyl chloride to give an intermediate N-carbonyl cycloalkyl compound which may be reduced with, for example, a hydride transfer agent. Compounds of the invention in which $R^4$ is a protected hydroxy group can be deprotected to give compounds in which $R^4$ is hydroxy. The choice of reagent may depend upon whether n is 0 or 1. For example an alkoxy or benzyloxy group can be deprotected by treatment with hydrogen bromide or borontribromide, by treating the alkoxy ether with diisobutylaluminium hydride or sodium propane thiolate or by subjecting the benzyloxy ether to hydrogenolysis. Where $R^4$ is an alkoxymethoxy group the protecting group may be removed with dilute acid. Compounds in which $R^4$ is hydroxy may be acylated to give compounds in which $R^4$ is acyloxy.

If in any of the processes described above the compound of the invention is obtained as an acid addition salt, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methane-sulphonic and p-toluenesulphonic acids.

The compounds of the invention possess one or more asymmetric carbon atoms and the compounds may be in the form of the pure enantiomorphs or mixtures of such enantiomorphs, such as racemates. When in the processes described herein a compound is defined by relative stereochemistry such as $1R^*, 2S^*, 6R^*$, it is to be understood that the compound can be in the form of pure enantiomorph possessing such relative stereochemistry or a mixture of enantiomorphs, e.g. a racemate, possessing this relative stereochemistry. Mixtures of diasteroisomers may be separated by chromatography) or fractional crystallisation. The ratio of the stereoisomers in the products or intermediates may be affected by the choice of reagent used in the process for preparing the compounds as exemplified above. Optical isomers may be prepared by resolving a racemic mixture by standard methods described in the literature. The racemate may be prepared by any of the processes outlined above. It is to be understood that the resolution may be carried out on the racemic mixture of the final desired product or it may be carried out on a racemic precursor of the desired compound provided further chemical reaction does not cause racemisation.

The starting materials of general formula (IV) may be prepared by the process illustrated below

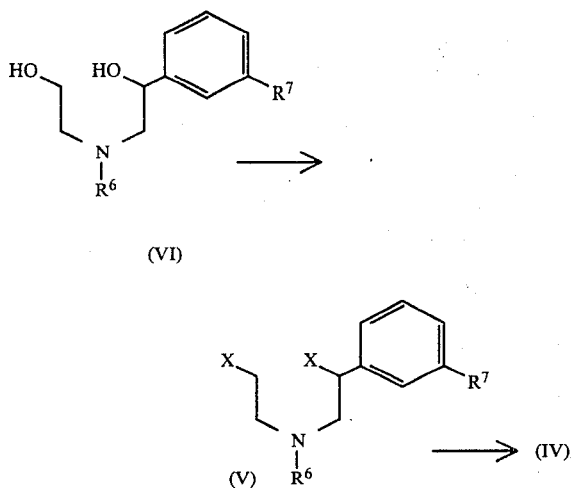

(in which $R^6$ and $R^7$ have the meaning given above and X is halogen, preferably chlorine or tosyl or mesyl). The starting diols of formula VI may be prepared by reacting an appropriate oxiran with an appropriate hydroxyalkylamine as described in our U.K. patent application No. 8,031,816 (Publication 2,061,272A). The diols of formula VI can then be converted to the compound of formula V by known methods (e.g. by treatment with a hydroxyl/halogen displacement reagent e.g. thionyl chloride or with a tosyl or mesyl halide) and the compound of formula V cyclised to the thiomorpholine of formula IV by reaction with an alkali metal sulphide (e.g. sodium sulphide). Preferably the cyclisation is effected in a solvent such as isopropanol/water or acetone/water.

The compounds of the invention possess pharmacological activity or are intermediates for other compounds of the invention having such activity. The compounds of the invention in which n is 0 and in which $R^4$ represents lower alkoxy, hydroxy or acyloxy in general possess analgesic activity and/or opiate antagonistic activity. For example 2R*, 6R*-2-ethyl-4,6-dimethyl-2-(3-hydroxyphenyl)-thiomorpholine, a representative compound of the invention, had an $ED_{50}$ of 5.2 mg/kg when administered subcutaneously to mice in a phenylbenzoquinone-induced writing test for analgesia based upon that of Proc. Soc. exp. Biol. Med., 1957, 95, 729 and had an $ED_{50}$ of less than 30 mg/kg subcutaneously in a procedure for opiate antagonistic activity based upon Aceto et al, Brit. J. Pharmac., 1969, 36, 225-239.

The compounds of the invention in which n is 1 and $R^4$ is hydrogen in general possess hypotensive or antihypotensive activity when tested in standard pharmacological testing procedures.

The invention provides a pharmaceutical composition comprising a compound of general formula (I) where n is 0 and $R^4$ is lower alkoxy, hydroxy or acyloxy or n is 1 and $R^4$ is hydrogen or a pharmaceutically acceptable acid addition salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, lactose, pectin, dextrin, starch, gelatin, tragacanth, methylcellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intra-muscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredients; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form. The following Examples illustrate the invention.

EXAMPLE 1

2-Chloro-N-(2-chloroethyl)-2-(3-methoxyphenyl)-N-methyl ethylamine

3-Methoxystyrene oxide (18 g) and N-methylethanolamine (9.4 ml) were placed in a 50 ml distillation flask; after 2 h a further portion of N-methylethanolamine (2 ml) was added and the reaction mixture left for 15 h at room temperature. The viscous oil was distilled in vacuo to yield N-(2-hydroxyethyl)-N-methyl-2-hydroxy-2-m-methoxyphenylethylamine (23.8 g) b.p. 178°–180° (at 1 m.b.)

The above diol (12.08 g) in CHCl$_3$ (750 ml) and DMF (5 ml) at 5° was treated dropwise with thionyl chloride (27 ml) and then heated to 55° for 1 h. The reaction mixture was cooled and extracted with water (3×250 ml). The aqueous phase was neutralised with sodium bicarbonate and extracted with CHCl$_3$ (3×200 ml). This extract was dried and the solvent removed in vacuo to yield an oil (8 g), which was treated with hydrochloric acid in ether, evaporated and the residue recrystallised twice from EtOH/EtOAc/Et$_2$O to yield the title compound as the hydrochloride (5 g) m.p. 128.5°–130°; (Found: C,48.0; H,6.1; N,4.9; calculated for C$_{12}$H$_{18}$Cl$_3$NO: C, 48.3; H,6.1; N,4.7).

EXAMPLE 2

2-(2-Methoxyphenyl)-4-methylthiomorpholine

2-Chloro-N-(2-chloroethyl)-2-(3-methoxyphenyl)-N-methylethylamine hydrochloride (2.98 g) in methanol (20 ml) was added dropwise, over 4 h, to a suspension of finely ground Na$_2$S.9H$_2$O (7.47 g) in acetone (25 ml). The reaction mixture was filtered, concentrated in vacuo, and partitioned between CH$_2$Cl$_2$ and H$_2$O. The ether phase was extracted with 2 N.HCl (2×) and this aqueous phase neutralised with NaHCO$_3$ and then extracted with CH$_2$Cl$_2$ (3×100 ml). After drying, HCl was bubbled through and then the solvent removed in vacuo. Recrystallisation from CH$_2$Cl$_2$/Et$_2$O yielded the title compound as the hydrochloride (1.7 g) m.p. 165°–166°; (Found: C,55.3; H,7.1; N,5.3; calculated for C$_{12}$H$_{17}$Cl$_2$NO.HCl: C,55.5; H,7.0; N,5.4).

EXAMPLE 3

2-(3-Hydroxyphenyl)-4-methylthiomorpholine 2-(3-Methoxyphenyl)-4-methylthiomorpholine hydrochloride (900 mg) in 50% HBr (15 ml) was refluxed for 3 h. The solution was neutralised with concentrated aqueous ammonia, extracted with CHCl$_3$ (3×50 ml) and the organic extract dried and concentrated in vacuo to yield an oil which on treatment with gaseous HCl in CH$_2$Cl$_2$ yielded the title compound hydrochloride (recrystallised from IPA/Et$_2$O); m.p. 164°; (Found: C,54.0; H,6.8; N,5.6; calculated for C$_{11}$H$_{16}$NOS.HCl: C,53.8; H,6.5; N,5.7).

EXAMPLE 4

1R*,2S*-2-(3-Methoxyphenyl)-4-methylthiomorpholine-1-oxide 2-(3-Methoxyphenyl)-4-methylthiomorpholine (1.03 g) in CHCl$_3$ (50 ml) was treated with 85% 3-chloroperbenzoic acid. After 1 h the mixture was poured into saturated NaHCO$_3$ solution, the layers were separated and the aqueous phase extracted with CHCl$_3$. After drying and removal of solvents in vacuo the residue was chromatographed on silica (70 g) using 10% MeOH in CHCl$_3$ as eluant. The relevant fractions were combined and evaporated in vacuo; the residue was crystallised from a small quantity of ether to yield the title compound, m.p. 68°–69.5°, (Found: C,60.5; H,7,4; N,6.0; calculated for C$_{12}$H$_{17}$NO$_2$S: C,60.2; H,7.2; N,5.85).

EXAMPLE 5

1R*,2R*-2-Ethyl-2-(3-methoxyphenyl)-4-methylthiomorpholine-1-oxide

1R*, 2S*-2-(3-methoxyphenyl)-4-methylthiomorpholine-1-oxide hydrochloride (6.6 g) in THF (100 ml) at −20° was treated with lithium diisopropylamide [ex. 1.6 M nBuLi (19.1 ml, and diisopropylamine (4 ml) in THF (75 ml)]. After 10 m (EtO)$_3$PO (5.1 ml) was added and the reaction allowed to warm to room temperature and then heated to 50° for 45 m. The reaction mixture was poured into brine (200 ml) and extracted with ether (3×200 ml). The organic extract was extracted with 2 N HCl (50 ml) and water (2×100 ml) and the extract was then neutralised with dil NaOH, and extracted with ether (2×200 ml). The organic extract was washed with brine, dried and the solvents removed in vacuo to yield an oil (5.35. g), which was chromatographed on silica (200 g) using 10% methanol in ether as eluant. The relevant fractions were combined and evaporated in vacuo to yield an oil (4.3 g) which on treatment with HCl in ether yielded the title compound hydrochloride; m.p. decomp>220°; (Found C,54.9; H,7.4; N,4.6; calculated for C$_{14}$H$_{21}$NO$_2$S.HCl: C,55.3; H,7.3; N,4.6).

EXAMPLE 6

1R*,2R*,6R*-4,6-Dimethyl-2-ethyl-2-(3-methoxyphenyl)thiomorpholine-1-oxide (1R*, 2R*-2-Ethyl-2-(3-methoxyphenyl)-4-methylthiomorpholine-1-oxide hydrochloride (3.97 g) in THF (100 ml) at 0° was treated with lithium diisopropylamide [ex 1.6 M nBuLi (10.5 ml) and diisopropylamine (2.4 l) in THF (50 ml)]. After 10 minutes, (MeO)$_3$PO (2.4 ml) was added and the reaction mixture immediately warmed to 30° for 1 h. The reaction mixture was poured into water (100 ml) and extracted with 2 N HCl (3×100 ml). The organic extract was extracted with 2 N HCl (3×50 ml) and the aqueous extract neutralised with concentrated aqueous ammonia and then extracted with ether (3×100 ml). This extract was washed with brine, dried and the solvent removed in vacuo to yield an oil which was chromatographed on silica (200 g) using 5% methanol in ether as eluant. The more polar component (1.0 g) was identical to the starting material. The less polar component was obtained as an oil (1.5 g) which on treatment with HCl in ether yielded the title compound as the hydrochloride, m.p. decomp>200°; (Found C,56.4; H,7.8; N,4.5; calculated for C$_{15}$H$_{23}$NO$_2$S.HCl:C,56.7; H,7.6; N,4.4).

EXAMPLE 7

2R*,6R*-4,6-Dimethyl-2-ethyl-2-(3-methoxyphenyl)-thiomorpholine

1R*, 2R*, 6R*-4,6-Dimethyl-2-ethyl-2-(3-methoxyphenyl) thiomorpholine-1-oxide hydrochloride (540 mg) and lithium aluminium hydride were suspended in dry ether (15 ml) at 0° and treated dropwise with TiCl$_4$ (0.3 ml). After 5 minutes the temperature was allowed to rise to room temperature and after a further 40 minutes, saturated NH$_4$Cl was added, followed by Na$_2$CO$_3$. The mixture was shaken with ether (50 ml) and filtered through kieselguhr. After two further extractions with Et$_2$O and CH$_2$Cl$_2$, the combined organic extract was washed with brine, dried and concentrated in vacuo to yield an oil which was chromatographed on silica using ether as eluant to yield an oil (360 mg) which gave the title compound hydrochloride as a solid on treatment with HCl in Et$_2$O; m.p. 199°-200°; (Found: C,59.9; H,8.2; N,4.9; calculated for C$_{15}$H$_{23}$NOS.HCl: C,59.7; H,8.0; N,4.6).

EXAMPLE 8

2R*, 6R*-4,6-Dimethyl-2-ethyl-2-(3-hydroxyphenyl)thiomorpholine

2R*, 6R*-4,6-Dimethyl-2-ethyl-2-(3-methoxyphenyl)thiomorpholine hydrochloride (300 mg) in 50% HBr (20 ml) was refluxed for 4h. The solution was basified with 5 N sodium hydroxide, extracted with ether (2×50 ml), and then extracted into 5 N hydrochloric acid. The aqueous extract was neutralised with solid Na$_2$CO$_3$ and finally extracted with ether (3×50 ml). The extract was dried and evaporated in vacuo to yield a solid, which on treatment with HCl in ether yielded the title compound as the hydrochloride, m.p. 150°-153° (resolidifies) and 234°-235°; (Found: C,58.2; H,7.8; N,4.8; calculated for C$_{14}$H$_{21}$NOS.HCl: C,58.4; H,7.7; N,4.9).

EXAMPLE 9

1R*, 2S*-2-Ethyl-2-(3-methoxyphenyl)-4-methyl thiomorpholine-1-oxide

1R*, 2S*-2-(3-methoxyphenyl)-4-methylthiomorpholine-1-oxide hydrochloride (5.3 g) in THF (100 ml) at −68° was treated with lithium diisopropylamide [ex 1.6 M nBuLi (16 ml) and diipropylamine (2.62 g) in THF (50 ml)] and stirred at −68° for 0.5 h. The temperature was raised to −30° and ethyl iodide (1.92 ml) was added and the temperature allowed to rise to 10° over 0.75 h and then briefly the temperature was raised to 30°. The reaction mixture was poured into water (150 ml) and extracted with ether (2×100 ml). The organic extract was extracted with 2 N HCl (3×50 ml). The aqueous phase was neutralised with NaHCO$_3$ and then extracted with ether (150 ml) and chloroform (3×150 ml). The extract was dried and the solvent removed in vacuo to yield an oil (5.5 g) which was chromatographed on silica in Et$_2$O/MeOH (5%) to give an oil (3.7 g), which was treated with HCl in ether. The solid so obtained was recrystallised from MeOH/CH$_2$Cl$_2$/Et$_2$O to yield the title compound as the hydrochloride; m.p. decomp>210°; (Found: C,55.6; H,7.6; N,4.7; calculated for C$_{14}$H$_{21}$NO$_2$S.HCl: C,55.35; H,7.25; N,4.6).

EXAMPLE 10

1R*, 2S*, 6R*-4,6-Dimethyl-2-ethyl-2-(3-methoxyphenyl)thiomorpholine-1-oxide 1R*, 2S*-2-Ethyl-4-methyl-2-(3-methoxyphenyl)thiomorpholine-1-oxide hydrochloride (2.34 g) in THF (50 ml) at −60° was treated with lithium diisopropylamide [ex. 1.6 M nBuLi (6.25 ml) and diisopropylamine (1.01 g) in THF (25 ml)], and then allowed to warm to 0° over 15 minutes. After recooling to −45°, methyl iodide (0.6 ml) was added and the reaction mixture allowed to warm to room temperature. After 30 minutes the mixture was poured into water (100 ml) and extracted with ether (3×50 ml). The organic extract was extracted with 2 N HCl (2×50 ml) and this extract was then neutralised with sodium bicarbonate and extracted with ether (3×100 ml). The extract was dried and the solvents removed in vacuo to yield an oil (2.57 g) which was chromatographed on silica (200 g) using 10% methanol in ether as eluant. The relevant fractions were combined and evaporated in vacuo to yield an oil (1.6 g), which on treatment with HCl in ether gave the title compound, hydrochloride, quarter hydrate m.p. decomp>245°; (Found: C,55.6; H,7.5; N,4.4; calculated for C$_{15}$H$_{23}$NO$_2$S.HCl.¼H$_2$O: C,55.9; H,7.6; N,4.3).

EXAMPLE 11

2R*, 6S*-4,6-Dimethyl-2-ethyl-2-(3-methoxyphenyl)thiomorpholine

The product of Example 10 (1.4 g) in CCl$_4$ (50 ml) was treated with triphenylphosphine (1.57 g) and refluxed for 2 h. After concentration in vacuo the residue was chromatographed on silica using ether/petrol 40°-60° as eluant to yield the title compound as an oil (850 mg) which was converted to the HCl salt; m.p. 238°; (Found: C,60.0; H,8.2; N,4.5; calculated for C$_{15}$H$_{23}$NOS.HCl: C, 59.7; H,8.0; N,4.6).

EXAMPLE 12

2R*, 6S*-2-Ethyl-4,6-dimethyl-2-(3-hydroxyphenyl)thiomorpholine

2R*, 6S*-4,6-Dimethyl-2-ethyl-2-(3-methoxyphenyl)-thiomorpholine (600 mg) was dissolved in aq.HBr (20 ml) and refluxed under nitrogen for 45 minutes. The reaction mixture was cooled, basified with concentrated aqueous ammonia and extracted with ether (3×50 ml). The extract was dried and evaporated in vacuo to yield an oil which crystallised on standing. Recrystallisation from ethyl acetate/40°-60° petrol yielded the title compound (500 mg); m.p. 114°-115°. The hydrochloride quarter hydrate salt was made in CH$_2$Cl$_2$; m.p. 265°-267°; (Found: C,57.9; H,7.7; N,4.6; calculated for C$_{14}$H$_{21}$NOS.HCl.¼H$_2$O: C,57.5; H,7.7; N,4.8).

EXAMPLE 13

2-Ethyl-2-(3-methoxyphenyl)-4-methylthiomorpholine

1R*, 2S*-2-Ethyl-2-(3-methoxyphenyl)-4-methylthiomorpholine-1-oxide hydrochloride (3.1 g) and triphenylphosphine (3.3 g) in CCl$_4$ (100 ml) were refluxed for 16 h. The reaction mixture was filtered through a silica pad and evaporated in vacuo and (C$_6$H$_5$)$_3$PO began to crystallise. From the mother liquors was isolated by chromatography (silica/ether) an oil (1.4 g) which on treatment with HCl in ether gave the title compound hydrochloride quarter hydrate m.p. 226°-227°; (Found: C,57.8; H,7.8; N,4.9; calculated for C$_{14}$H$_{21}$NOS.HCl.¼H$_2$O: C,57.5; H,7.7; N,4.8)

EXAMPLE 14

2-Ethyl-2-(3-hydroxyphenyl)-4-methylthiomorpholine

The product of Example 13 (1.0 g) in 50% HBr was refluxed for 2 h, concentrated in vacuo and then neutralised with concentrated aqueous ammonia. The product was extracted into ether (2×100 ml), washed with brine, dried and concentrated in vacuo to yield a foam (800 mg) which on treatment with tosic acid monohydrate in ether gave the title compound as the p-toluene sulfonate salt. (Found: C,58.8; H,6.6; N,3.5; calculated for $C_{13}H_{19}NOS \cdot C_7H_8SO_3$: C,58.7; H,6.6; N,3.4).

EXAMPLE 15

1R*,2R*-2-Ethyl-4-methyl-2-phenylthiomorpholine-1-oxide

1R*,2S*-4-Methyl-2-phenylthiomorpholine-1-oxide (5.4 g) in THF (50 ml) at 0° was treated with lithium diisopropylamide [ex. 1.6 M n-butyllithium (19.4 ml) and diisopropylamine (4.3 ml)]. After 10 minutes $(EtO)_3PO$ (5.3 ml) was added and the solution immediately warmed to 30°. After 1.5 h the reaction mixture was poured into water (100 ml) and extracted with ether (3×100 ml). The organic phase was washed with water and then extracted with 2 N HCl (2×50 ml). This aqueous extract was neutralised with $Na_2CO_3$ and extracted with ether (1×100 ml) and chloroform (3×100 ml). The combined organic extract was washed with brine, dried and the solvent removed in vacuo to yield an oil (8 g), which was chromatographed on $SiO_2$ (250 g) using 5% MeOH in ethyl acetate as eluant. The relevant fractions were combined and evaporated in vacuo to yield an oil (2.4 g) which on treatment with HCl in ether gave the title compound as the hydrochloride (recrystallised from $CHCl_3/Et_2O$); m.p. decomp 220°; (Found: C, 57.1; H, 7.4; N, 4.9; calculated for $C_{13}H_{19}NOS \cdot HCl$. C, 57.0; H, 7.4; N, 5.1).

EXAMPLE 16

1R*,2R*,6R*-4,6-Dimethyl-2-ethyl-2-phenylthiomorpholine-1-oxide

1R*,2R*-2-Ethyl-4-methyl-2-phenylthiomorpholine-1-oxide hydrochloride (1.5 g) in THF (10 ml) was added to lithium diisopropylamide [ex. 1.6 M n-buthyllithium (5.2 ml) and diisopropylamine (1.2 ml)] in THF (25 ml) at 0°. After 5 minutes $(MeO)_3PO$ (0.93 ml) was added and the reaction mixture was warmed to 40°. After 20 minutes the reaction mixture was poured into water and extracted with ether (3×). The organic phase was extracted with 2 N HCl (2×) and this aqueous phase was washed with ether and then neutralised with sodium carbonate. After extraction into ether (3×), the extract was washed with brine, dried and evaporated in vacuo to yield an oil (1.8 g). Chromatography on $SiO_2$ in 5% methanol in ethyl acetate yielded the free base title compound (mp 68-72) which was converted to the hydrochloride quarter hydrate and crystallised from $CHCl_3/Et_2O$; m.p. decomp 200°; (Found, C, 57.8; H, 7.6; N, 4.6; calculated for $(C_{14}H_{21}NOS \cdot HCl \cdot \frac{1}{4}H_2O$; C, 57.5; H, 7.8; N, 4.8).

EXAMPLE 17

1R*,2S*-2-Ethyl-4-methyl-2-phenylthiomorpholine-1-oxide

1R*,2S*-4-methyl-2-phenylthiomorpholine-1-oxide (8 g) in THF (50 ml) was added to lithium diisopropylamide [ex. 1.55 M n-butyllithium (25.8 ml) and diisopropylamine (5.3 ml) in THF (100 ml)] at 5° C. After 10 minutes ethyl iodide (3.2 ml) was added and after ½ hour at room temperature the reaction mixture was worked up as in Example 15. Chromatography on $SiO_2$ in 10% methanol in chloroform yielded pure title compound (1.6 g) which was converted to the hydrochloride and recrystallised from IPA/MeOH/$Et_2O$; m.p. decomp>225°; (Found, C, 56.8; H, 7.5; N, 4.8; calculated for $C_{13}H_{19}NOS \cdot HCl$, C, 57.0; H, 7.4; N, 5.1).

EXAMPLE 18

1R*,2S*,6R*-2-Ethyl-4,6-dimethyl-2-phenylthiomorpholine-1-oxide

1R*,2S*-2-Ethyl-4-methyl-2-phenylthiomorpholine-1-oxide (1.5 g) in THF (20 ml) at 0° was treated with lithium diisopropylamide [ex 1.6 M n-butyllithium (4.3 ml) and diisopropylamine (0.95 ml) in THF (30 ml)]. To the red solution was added $(MeO)_3PO$ (0.8 ml) and after 10 minutes the reaction mixture was warmed to 30°. After 1 hour the reaction mixture was poured into water (100 ml) and extracted with ether (3×100 ml). The organic extract was extracted with 2 N HCl (2×50 ml) and this extract neutralised with sodium carbonate and then extracted with ether (3×100 ml). The organic extract was dried and the solvent removed in vacuo to yield an oil which was chromatographed on $SiO_2$ using ether as eluant. The relevant fractions were combined and evaporated in vacuo to yield an oil (430 mg) which on treatment with HCl in $Et_2O$ gave the title compound as the hydrochloride, m.p. decomp 200°; (Found: C, 58.2; H, 7.7; N, 4.8; calculated for $C_{14}H_{21}NOS \cdot HCl$.; C, 58.4; H, 7.7; N, 4.9).

EXAMPLE 19

1R*,2S*-2,4-Dimethyl-2-phenylthiomorpholine-1-oxide

1R*,2S*-4-methyl-2-phenylthiomorpholine-1-oxide (840 mg) in THF (5 ml) was added to lithium diisopropylamide [from n-butyl lithium 1.6 M in hexane (2.7 ml) and diisopropylamine (0.58 ml) in THF (15 ml)] at 5° C. Trimethyl phosphate (0.47 ml) was added and the reaction slowly heated to 30° C. After 1 hour the reaction mixture was poured onto water and extracted with ether (3×25 ml). The organic extract was extracted with 2 N HCl (3×25 ml) and this extract neutralised with sodium carbonate and again extracted with ether 3×25 ml). The extract was dried ($MgSO_4$) and solvent removed in vacuo to yield an oil which was chromatographed on silica using 10% methanol on ether. The product was isolated as its hydrochloride salt affording 200 mg of the title compound as the hydrochloride, m.p. decomp about 220°.

(Found C, 54.65; H, 7.2; N, 5.1; $C_{12}H_{17}NOS \cdot HCl\frac{1}{4}H_2O$ requires C, 54.5; H, 7.0; N, 5.3%).

We claim:

1. A compound selected from the group consisting of a thiomorpholine of formula (I)

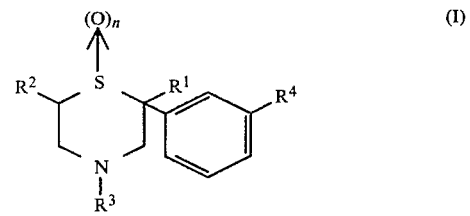

and a pharmaceutically acceptable acid addition salt thereof, wherein n represents 0 or 1, $R^1$ represents (lower)alkyl, $R^2$ represents hydrogen or (lower)alkyl, $R^3$ represents hydrogen, lower alkyl, lower alkenyl, lower alkynyl, phenyl(lower)alkyl, 2-tetrahydrofurylmethyl or cycloalkylmethyl and $R^4$ represents hydrogen, hydroxy, lower alkanoyloxy, lower alkoxy, benzyloxy, or (lower)alkoxymethoxy, with the proviso that when n is 0, $R^4$ is other than hydrogen.

2. A compound as claimed in claim 1 which is a thiomorpholine of formula (Ia)

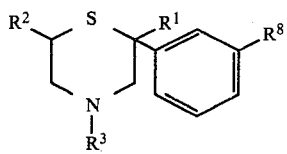

or a pharmaceutically acceptable acid addition salt thereof, wherein $R^1$ represents (lower)alkyl, $R^2$ represents hydrogen or (lower)alkyl, $R^3$ represents hydrogen, lower alkyl, lower alkenyl, lower alkynyl, phenyl(lower)alkyl, 2-tetrahydrofurylmethyl or cycloalkylmethyl and $R^8$ represents hydroxy, lower alkanoyloxy, lower alkoxy, benzyloxy, or (lower)alkoxymethoxy.

3. A compound as claimed in claim 1 which is a thiomorpholine of formula (Ia)

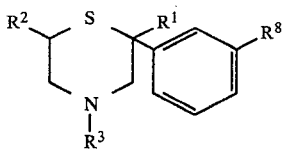

or a pharmaceutically acceptable acid addition salt thereof, wherein $R^1$ represents (lower)alkyl, $R^2$ represents hydrogen or (lower)alkyl, $R^3$ represents hydrogen, lower alkyl, lower alkenyl, lower alkynyl, phenyl(lower)alkyl, 2-tetrahydrofurylmethyl or cycloalkylmethyl and $R^8$ represents hydroxy, lower alkanoyloxy or lower alkoxy.

4. A compound as claimed in claim 1 which is 2R*,6R*-4,6-dimethyl-2-ethyl-2-(3-methoxyphenyl)thiomorpholine or a pharmaceutically acceptable acid addition salt thereof.

5. A compound as claimed in claim 1 which is 2R*,6R*-4,6-dimethyl-2-ethyl-2-(3-hydroxyphenyl)-thiomorpholine or a pharmaceutically acceptable acid addition salt thereof.

6. A compound as claimed in claim 1 which is 2R*,6S*-4,6-dimethyl-2-ethyl-2-(3-methoxyphenyl)thiomorpholine or a pharmaceutically acceptable acid addition salt thereof.

7. A compound as claimed in claim 1 which is 2R*,6S*-2-ethyl-4,6-dimethyl-2-(3-hydroxyphenyl)thiomorpholine or a pharmaceutically acceptable acid addition salt thereof.

8. A compound as claimed in claim 1 which is 2-ethyl-2-(3-methoxyphenyl)-4-methylthiomorpholine or a pharmaceutically acceptable acid addition salt thereof.

9. A compound as claimed in claim 1 which is 2-ethyl-2-(3-hydroxyphenyl)-4-methylthiomorpholine or a pharmaceutically acceptable acid addition salt thereof.

10. A compound as claimed in claim 1 which is a thiomorpholine of formula (Ib)

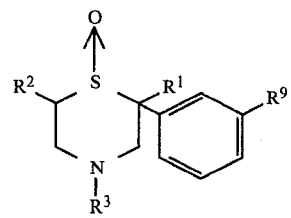

or a pharmaceutically acceptable salt thereof, wherein $R^1$ represents (lower)alkyl, $R^2$ represents hydrogen or (lower)alkyl, $R^3$ represents hydrogen, lower alkyl, lower alkenyl, lower alkynyl, phenyl(lower)alkyl, 2-tetrahydrofurylmethyl or cycloalkylmethyl and $R^9$ represents hydrogen, hydroxy, lower alkanoyloxy, lower alkoxy, benzyloxy, or (lower)alkoxymethoxy.

11. A compound as claimed in claim 10 wherein $R^9$ represents hydrogen.

12. A compound as claimed in claim 1 which is 1R*,2R*-2-ethyl-4-methyl-2-phenylthiomorpholine-1-oxide or a pharmaceutically acceptable acid addition salt thereof.

13. A compound as claimed in claim 1 which is 1R*,2R*,6R*-4,6-dimethyl-2-ethyl-2-phenylthiomorpholine-1-oxide or a pharmaceutically acceptable acid addition salt thereof.

14. A compound as claimed in claim 1 which is 1R*,2S*-2-ethyl-4-methyl-2-phenylthiomorpholine-1-oxide or a pharmaceutically acceptable acid addition salt thereof.

15. A compound as claimed in claim 1 which is 1R*,2S*,6R*-2-ethyl-4,6-dimethyl-2-phenylthiomorpholine-1-oxide or a pharmaceutically acceptable acid addition salt thereof.

16. An analgesic or opiate antagonist pharmaceutical composition comprising a compound as claimed in claim 1 wherein n is 0 and $R^4$ is lower alkoxy, hydroxy or lower alkanoyloxy or n is 1 and $R^4$ is hydrogen in association with a pharmaceutically acceptable carrier.

17. A method of treating a mammal in need of an analgesic or opiate antagonist which comprises administering to said mammal an analgesically or opiate antagonistically effective amount of a compound selected from the group consisting of a thiomorpholine of formula (Ia)

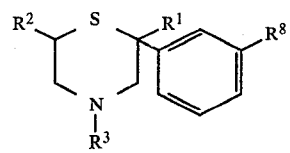

and a pharmaceutically acceptable acid addition salt thereof, wherein $R^1$ represents (lower)alkyl, $R^2$ represents hydrogen or (lower)alkyl, $R^3$ represents hydrogen, lower alkyl, lower alkenyl, lower alkynyl, phenyl(lower)alkyl, 2-tetrahydrofurylmethyl or cycloalkylmethyl and $R^8$ represents hydroxy, lower alkanoyloxy or lower alkoxy.

* * * * *